United States Patent
Hassanein et al.

(10) Patent No.: US 7,572,622 B2
(45) Date of Patent: Aug. 11, 2009

(54) HEART PRESERVATION CHAMBER

(75) Inventors: Waleed H. Hassanein, North Andover, MA (US); Richard L. Bringham, North Andover, MA (US); Ronald L. Taylor, Jr., Everett, MA (US)

(73) Assignee: TransMedic, Inc., Andover, MA (US)

( * ) Notice: Subject to any disclaimer, the term of this patent is extended or adjusted under 35 U.S.C. 154(b) by 566 days.

(21) Appl. No.: 10/640,867

(22) Filed: Aug. 14, 2003

(65) Prior Publication Data

US 2004/0171138 A1 Sep. 2, 2004

Related U.S. Application Data

(60) Provisional application No. 60/403,556, filed on Aug. 14, 2002.

(51) Int. Cl.
*A01N 1/02* (2006.01)
(52) U.S. Cl. .................. 435/284.1; 435/1.2
(58) Field of Classification Search .............. 435/284.1, 435/1.2; 15/257.06; 220/570; 396/631, 396/641, 643
See application file for complete search history.

(56) References Cited

U.S. PATENT DOCUMENTS

| | | | |
|---|---|---|---|
| 3,406,531 A | 10/1968 | Swenson et al. | |
| 3,468,136 A | 9/1969 | Swenson et al. | |
| 3,545,221 A | 12/1970 | Swenson et al. | |
| 3,545,605 A * | 12/1970 | Robbins | 206/223 |
| 3,607,646 A | 9/1971 | De Roissart | |
| 3,632,473 A | 1/1972 | Belzer et al. | |
| 3,654,085 A | 4/1972 | Norr et al. | |
| 3,738,914 A | 6/1973 | Thorne et al. | |
| 3,772,153 A | 11/1973 | De Roissart | |
| 3,777,507 A | 12/1973 | Burton et al. | |
| 3,843,455 A * | 10/1974 | Bier | 435/284.1 |
| 3,881,990 A | 5/1975 | Burton et al. | |
| 3,995,444 A | 12/1976 | Clark et al. | |
| 4,186,565 A | 2/1980 | Toledo-Pereyra | |
| 4,723,939 A | 2/1988 | Anaise | |
| 4,745,759 A | 5/1988 | Bauer et al. | |
| 5,051,352 A | 9/1991 | Martindale et al. | |
| 5,157,930 A | 10/1992 | McGhee et al. | |
| 5,326,706 A | 7/1994 | Yland et al. | |
| 5,339,662 A | 8/1994 | Goldman | |
| 5,356,771 A | 10/1994 | O'Dell | |
| 5,362,622 A | 11/1994 | O'Dell et al. | |
| 5,395,314 A | 3/1995 | Klatz et al. | |
| 5,472,876 A | 12/1995 | Fahy | |

(Continued)

FOREIGN PATENT DOCUMENTS

EP 0 376 763 7/1990

(Continued)

OTHER PUBLICATIONS

Eiseman, B. et al., "A Disposable Liver Perfusion Chamber," *Surgery*, 60:1183-1186 (1966).

*Primary Examiner*—William H Beisner
(74) *Attorney, Agent, or Firm*—Hamilton, Brook, Smith & Reynolds, P.C.

(57) ABSTRACT

A heart preservation chamber is disclosed which comprises a housing, an inclined trough support surface, and inlet and outlet fluid connections for the major heart blood vessels.

37 Claims, 3 Drawing Sheets

U.S. PATENT DOCUMENTS

| | | | |
|---|---|---|---|
| 5,473,791 A * | 12/1995 | Holcomb et al. | 15/230.11 |
| 5,494,822 A | 2/1996 | Sadri | |
| 5,584,804 A | 12/1996 | Klatz et al. | |
| 5,586,438 A * | 12/1996 | Fahy | 62/78 |
| 5,716,378 A | 2/1998 | Minten | |
| 5,752,929 A | 5/1998 | Klatz et al. | |
| 5,786,136 A | 7/1998 | Mayer | |
| 5,787,544 A * | 8/1998 | Meade | 15/257.06 |
| 5,807,737 A | 9/1998 | Schill et al. | |
| 5,856,081 A | 1/1999 | Fahy | |
| 5,965,433 A | 10/1999 | Gardetto et al. | |
| 6,024,698 A | 2/2000 | Brasile | |
| 6,046,046 A * | 4/2000 | Hassanein | 435/284.1 |
| 6,100,082 A | 8/2000 | Hassanein et al. | |
| 6,673,594 B1 * | 1/2004 | Owen et al. | 435/284.1 |
| 2002/0012988 A1 | 1/2002 | Brasile | |
| 2003/0074760 A1 * | 4/2003 | Keller | 15/230.11 |

FOREIGN PATENT DOCUMENTS

| | | |
|---|---|---|
| WO | WO 88/05261 | 7/1988 |
| WO | WO 97/46091 | 12/1997 |
| WO | WO 99/15011 | 4/1999 |
| WO | WO 00/60936 | 10/2000 |

* cited by examiner

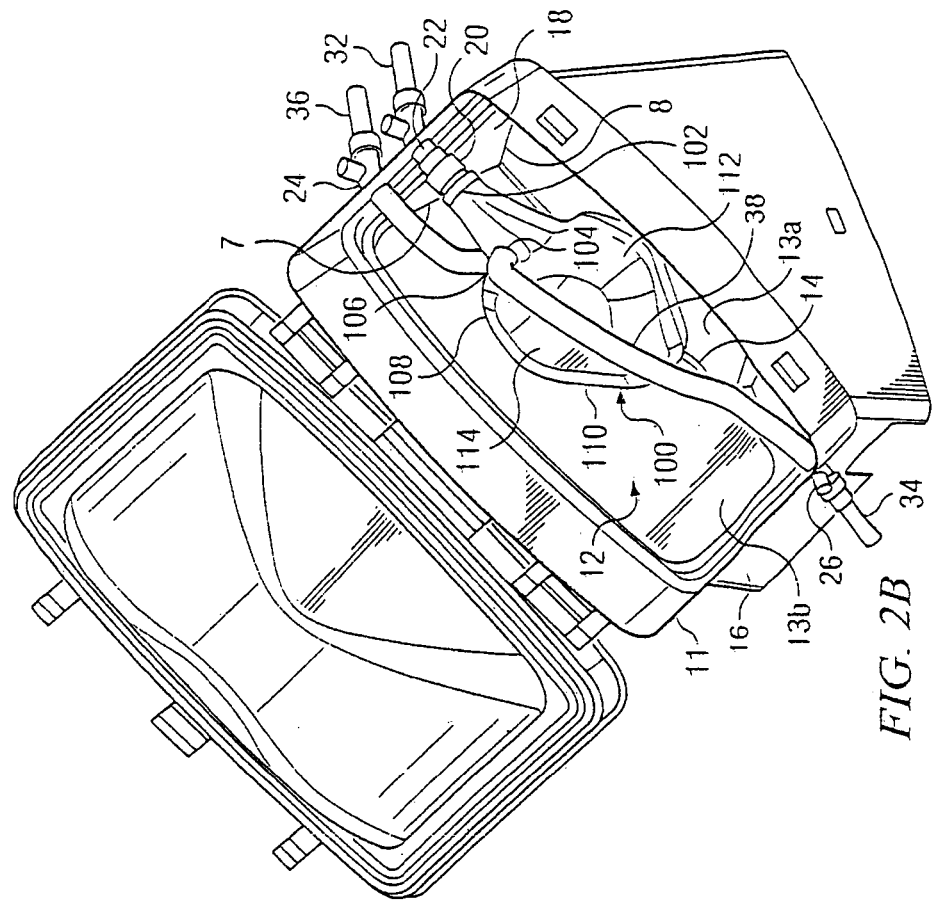
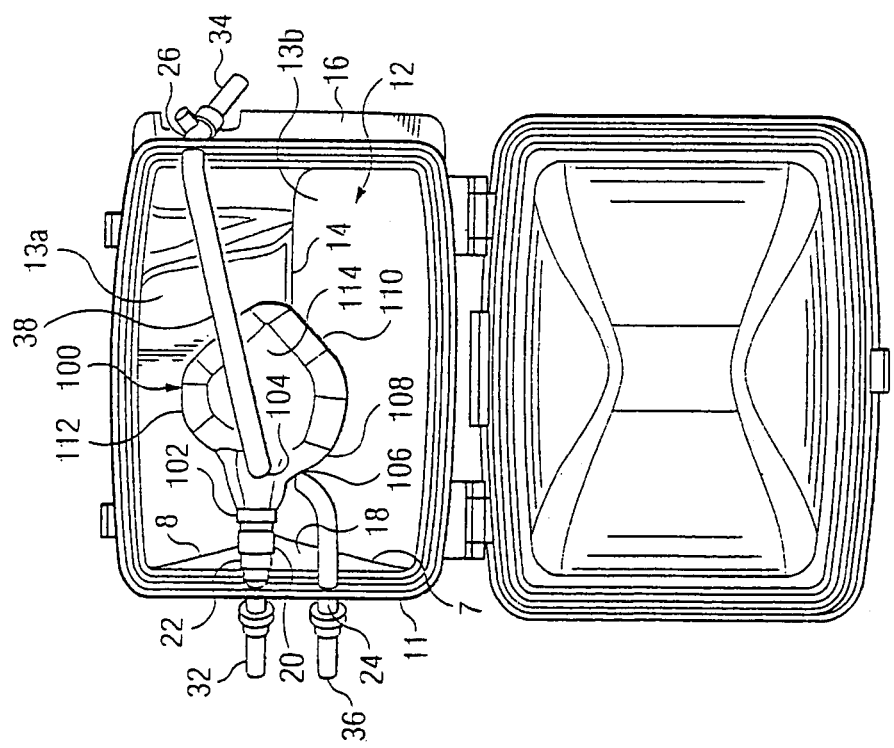
FIG. 2A
FIG. 2B

HEART PRESERVATION CHAMBER

RELATED APPLICATION

This application claims the benefit of U.S. Provisional Application No. 60/403,556, filed Aug. 14, 2002. The entire teachings of the above application is incorporated herein by reference.

BACKGROUND OF THE INVENTION

This application relates to the field of heart preservation, resuscitation, evaluation and maintenance.

Organ preservation devices, such as the POPS™ system designed by TransMedics, Inc., often require a specially designed chamber to house the organ. Examples of such organ preservation devices are described in U.S. Pat. Nos. 6,046,046 and 6,100,082, the entire teachings of which are incorporated herein by reference.

Recent advances in the field of organ preservation have led to a desire to have the organ kept in a functioning and viable state during the preservation period. To do so, the organ must be maintained in a way that allows it to so function. Previous containers for the heart have been constructed to have the heart suspended from the cannulas which deliver blood to and take blood away from the heart's arterial and venous vessels, respectively. However, such suspension of the heart by its vessels can cause problems of aorta tearing and heart ischemia over long periods of time. Alternatively, previous containers and methods have allowed the heart to lay on a flat surface. These devices have led to a lack of tension on the aortic root which interferes with the competency of the heart valve leaflets. Again, ischemic tissue results.

SUMMARY OF THE INVENTION

The heart preservation apparatus 10 of the present invention allows a heart 100 to be housed in a chamber (i.e. container) which permits it to continue beating and pumping blood through all of its chambers and vessels. This is accomplished by providing cannulas that are inserted into the aorta 102, pulmonary artery 104, and pulmonary vein(s) 106.

The heart preservation apparatus 10 of the present invention also solves the problems of prior organ chambers which suspend the heart by its vessels or allow it to lay on a flat surface. The present chamber has an inclined support surface 13a and inclined support surface 13b which meet at a chamber base 14, forming an inclined trough 12. The inclined trough has a concave cross-sectional shape along an axis of the chamber 10, in which the concave cross-sectional shape can be v-shaped or u-shaped. The v-shape is depicted at the point where the inclined surfaces 13a and 13b meet an upper wall 18 at junctions 7 and 8. The inclined trough 12 provides the optimal balance between supporting the heart 100 and maintaining aortic valve competence. The heart 100 rests on the inclined trough 12 and is cannulated through the aorta 102, pulmonary artery 104, and pulmonary vein(s) 106. The cannulation of the aorta 102 helps maintain aortic valve competency, while the incline support of the organ allows a significant portion of the organ's weight to be supported by the support surface and not by the cannulated vessels.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 2A-2D are a diagram of the heart preservation chamber in an open position.

DETAILED DESCRIPTION OF THE INVENTION

Figure 1B:
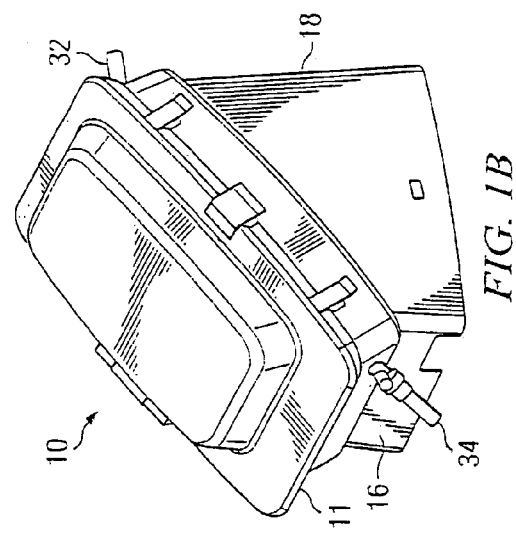
FIGS. 1A-1D are a diagram of the heart preservation chamber in a closed position.
Figure 1D:
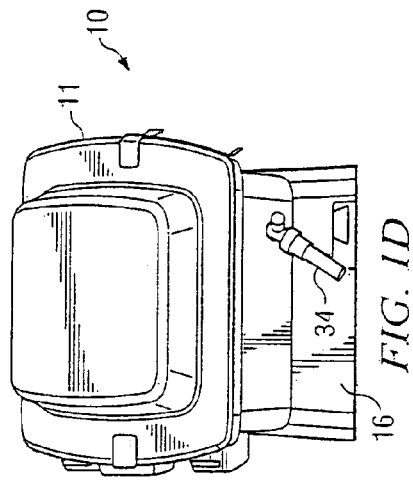
Figure 1A:
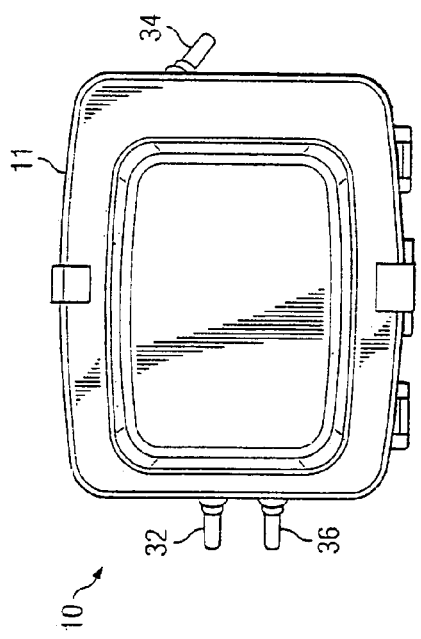
Figure 1C:
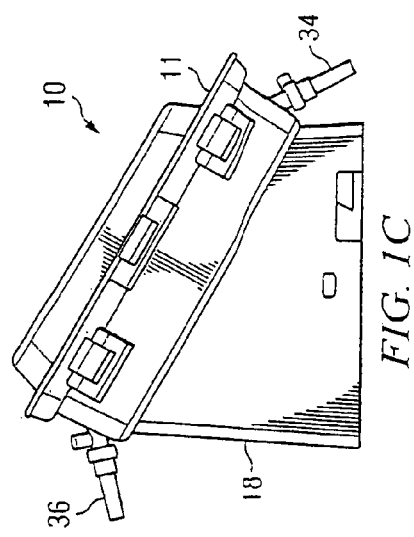
Figure 2C:
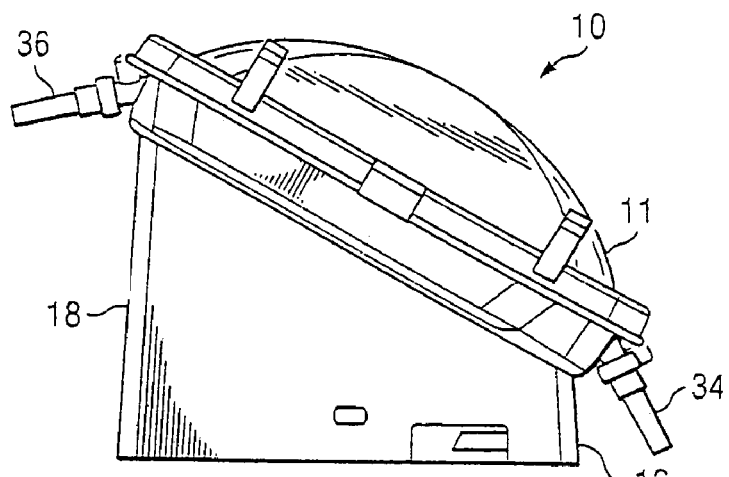
Figure 2D:
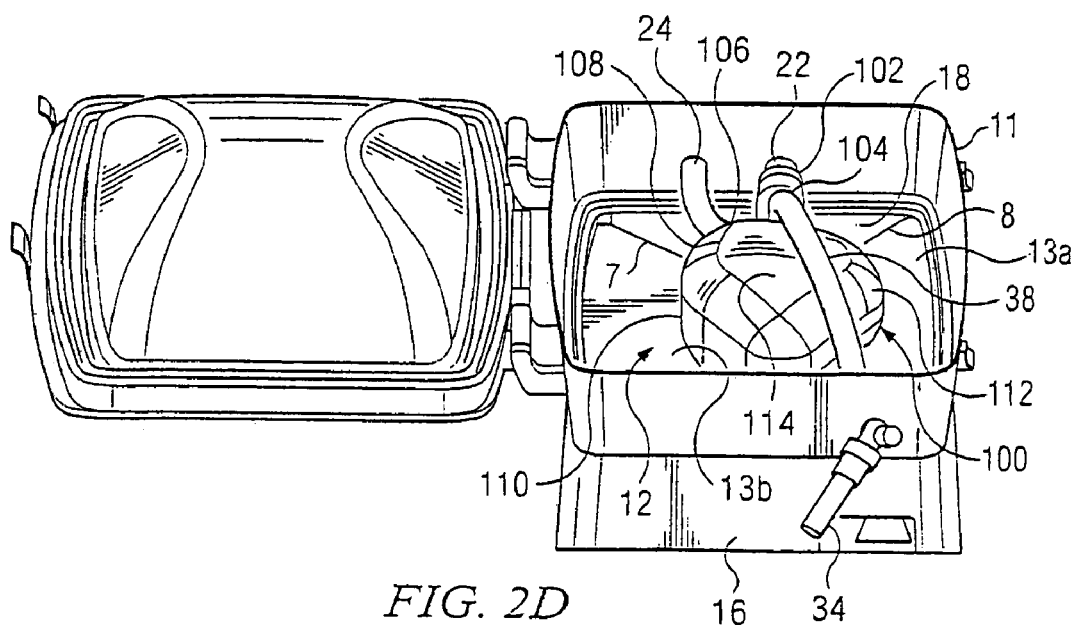

A description of preferred embodiments of the invention follows.

The heart preservation apparatus 10 comprises a housing 11 defining a chamber that typically is at least partially transparent, has an inclined trough 12, preferably v-shaped, for supporting the heart 100, and includes a connector 22 for the aorta 102 attached to the upper wall 18 of the apparatus 10, at least one other inlet means 24 attached to the upper wall 18 and at least one other outlet means 26, attached to a lower wall 16, through the walls of the chamber for connecting fluid from or to a preservation fluid circuit to the heart 100. Sterilized cable straps 20 tighten around the heart blood vessels, to the connectors, creating a leakproof seal with the chamber. In a preferred embodiment, the heart preservation apparatus 10 provides a sterile sealed, warm, moist environment for preserving and maintaining a viable, functioning heart 100.

The housing 11 typically is at least partially transparent to allow the heart 100 to be viewed during the preservation period. The inclined support surface 13a and the inclined support surface 13b meet at the chamber base 14 to form an inclined support trough 12, preferably v-shaped, for the heart 100, that provides lateral support for the heart 100 during transportation. The v-shape is depicted where the inclined surfaces 13a and 13b meet the upper wall 18 at junctions 7 and 8. The cannulation of the heart's vessels 102, 104, 106 serves to deliver to and take fluid away from the heart 100, provide tension on the aorta 102 to maintain aortic valve competence, as well as to provide some support of the heart's weight. The cannulas 32, 34, 36, 38 may be physically embedded in the upper wall 18 and lower wall 16 of the heart preservation apparatus 10. Placing tension on the aorta 102 serves to maintain aortic valve competency. However, the use of the inclined trough 12 causes a reduction in the tension under which the aorta 102 is placed since much of the weight of the heart 100 is supported by the inclined trough 12. Compared to a heart 100 vertically suspended by the aorta 102, this results in less stress on the aorta 102 which lessens the damage to the aorta 102 itself, reduces the chance of the aorta 102 detaching from the aorta connector (cannula) 22 during use, results in a shorter and more compact organ chamber 10 that reduces the weight and size of a preservation system for transport, and gives the heart 100 mechanical support to keep it from swinging and otherwise moving during transport. In addition, suspension of the heart 100 at 90 degrees (vertically) will interfere with the diameter of the coronary Ostia (the inlet of the coronary vessels) and thus may interfere with the blood volume perfusing the heart 100 resulting in an ischemic organ (lack of blood supply).

A problem with placing the heart 100 in a horizontal position is that the resulting lack of tension on the aortic root will interfere with the leaflets' competency. This will result in aortic valve incompetence and will decrease, if not eliminate, the coronary blood flow. This will result in ischemia to the preserved organ 100 and damage to the myocardial tissue. In addition to valve problems, placing the heart 100 horizontally on a flat surface may place pressure on the surface coronary vessels (Left Anterior Descending (LAD) or Posterior Descending (PDA) arteries) which will prevent blood supply to either the anterior or posterior heart surfaces, respectively. A horizontal position also does not facilitate fluid drainage away from the heart 100.

The heart 100 is preserved in two modes: a beating-non-working mode and a beating-working mode. In one embodiment of the procedure, the heart 100 is perfused first in the beating-non-working state for 5-10 minutes while all the cannulation takes place. Then, the heart 100 is switched to the beating-working mode. This allows the heart 100 to then pump blood in a physiologic fashion.

In the beating-non-working mode, a mechanical pump pumps blood to the aorta 102 (in an opposite direction to physiologic flow) to perfuse the coronary vessels. The mechanical pump through the left atrial cannula 36 will trickle blood to the left atrium 108 to supply oxygenated blood to fill the left chambers 108, 110. The right side 112 of the heart 100 still pumps the coronary flow out towards the pulmonary artery 104 and the fluid is collected through a cannula 38.

In the beating-working mode, a mechanical pump pumps the blood to the left atrium 108 to fill the heart 100. In this case, the heart 100 muscle pumps the blood from the left ventricle 110 to the aorta 102 and the heart 100 itself pumps the coronary flow. The right side 112 of the heart 100 pumps the returned coronary flow to the pulmonary artery 104, where there is a cannula 38 to return the blood to the fluid reservoir.

The inclined support surface 13a and inclined support surface 13b meet at the chamber base 14 to form an inclined trough 12 which supports the heart 100. This serves to (1) eliminate excessive tension on the aortic tissue while maintaining enough tension to maintain aortic valve competency; (2) provide stability to the heart during transportation; and (3) provide for fluid drainage away from the heart 100. These functions can also be performed by a V- or U-shaped groove. In the preferred embodiment, the heart 100 rests on the inclined trough 12 with the posterior side 114 facing up.

While this invention has been particularly shown and described with references to preferred embodiments thereof, it will be understood by those skilled in the art that various changes in form and details may be made therein without departing from the scope of the invention encompassed by the appended claims.

What is claimed is:

1. A heart preservation apparatus comprising:
a housing defining a chamber;
an inclined trough, having a concave cross-sectional shape along an axis of the chamber, said trough having an upper end and a lower end, to support a heart between the upper and lower ends of the inclined trough; and
a connector in fluid communication with the heart and coupled to the housing at the upper end of the inclined trough and coupled to the aorta of the heart in a manner placing tension on the aorta to maintain competency of the aortic valve within the heart.

2. A heart preservation apparatus according to claim 1 wherein the inclined trough is inclined to an angle between about 10 degrees and about 80 degrees.

3. A heart preservation apparatus according to claim 1 wherein the inclined trough is inclined to an angle of about 30 degrees.

4. A heart preservation apparatus according to claim 1 wherein the inclined trough supports between 10% and 90% of the heart's weight.

5. A heart preservation apparatus according to claim 1 further comprising at least one additional connector, wherein the at least one additional connector is configured to be connected to at least one vessel selected from a group consisting of: a pulmonary artery and a pulmonary vein.

6. A heart preservation apparatus according to claim 5 wherein the at least one additional connector configured to be connected to the pulmonary artery connects to a lower end of the inclined trough.

7. A heart preservation apparatus according to claim 5 wherein the at least one additional connector configured to be connected to the pulmonary vein connects to an upper end of the inclined trough.

8. A heart preservation apparatus according to claim 1 further comprising a cover which, when in a closed position, combines with the housing to provide a sterile sealed enclosure.

9. A heart preservation apparatus according to claim 1 wherein the housing is made from a biocompatible polymer.

10. A heart preservation apparatus according to claim 1 wherein the at least one connector connects through a wall of the chamber to a perfusion circuit.

11. A heart preservation apparatus according to claim 1 wherein the concave cross-sectional shape of the inclined trough is v-shaped.

12. A heart preservation apparatus according to claim 1 wherein the concave cross-sectional shape of the inclined trough is u-shaped.

13. A heart preservation apparatus according to claim 1 wherein the inclined trough is defined by at least one wall that has an upper and a lower end-and wherein the at least one connector is coupled to the at least one wall at or proximal to the upper end of the wall.

14. A heart preservation apparatus according to claim 1 wherein the housing is defined by at least one wall that has an upper and a lower end and wherein the at least one-connector is coupled to the at least one wall at or proximal to the upper end of the wall.

15. A heart preservation apparatus according to claim 1 wherein the housing is at least partially transparent.

16. A heart preservation apparatus, comprising:
a housing defining a chamber;
an inclined trough within the chamber having a concave cross-sectional shape to support a heart within the chamber, the inclined trough having an upper end and a lower end; and
a cannula configured to be coupled to an aorta of the heart supported by the inclined trough and coupled to the housing at the upper end of the inclined trough to align the aorta-to-apex axis of the heart with an axis of the inclined trough and to place tension on the aorta to maintain competency of an aortic valve within the heart.

17. A heart preservation apparatus according to claim 16 wherein the housing is at least partially transparent.

18. A heart preservation apparatus according to claim 16 wherein the inclined trough is inclined to an angle of (i) about 10 degrees and about 80 degrees or (ii) about 30 degrees.

19. A heart preservation apparatus according to claim 16 further comprising at least one additional cannula, wherein the at least one additional cannula is configured to be connected to at least one vessel selected from a group consisting of: a pulmonary artery and a pulmonary vein.

20. A heart preservation apparatus according to claim 19 wherein the at least one additional cannula configured to be connected to the pulmonary artery connects to a lower end of the inclined trough and wherein the at least one additional cannula configured to be connected to the pulmonary vein connects to an upper end of the inclined trough.

21. A heart preservation apparatus according to claim 16 further comprising a cover which, when in a closed position, combines with the housing to provide a sterile sealed enclosure.

22. A heart preservation apparatus according to claim 16 wherein the concave cross-sectional shape of the inclined trough is v-shaped or u-shaped.

23. A heart preservation apparatus comprising:
a housing defining a chamber;
an inclined trough, having a concave cross-sectional shape along an axis of the chamber, said trough having an upper end and a lower end, to support a heart between the upper and lower ends of the inclined trough; and
a connector coupled to the housing proximal to the upper end of the inclined trough and coupled to the aorta of the heart to align the aorta-to-apex axis of the heart with an axis of the inclined trough, in a manner placing tension on the aorta while in fluid communication with the heart to maintain competency of the aortic valve within the heart.

24. A heart preservation apparatus according to claim 23 wherein the housing is at least partially transparent.

25. A heart preservation apparatus according to claim 23 wherein the inclined trough is inclined to an angle between about 10 degrees and about 80 degrees.

26. A heart preservation apparatus according to claim 23 wherein the inclined trough is inclined to an angle of about 30 degrees.

27. A heart preservation apparatus according to claim 23 wherein the inclined trough supports between 10% and 90% of the heart's weight.

28. A heart preservation apparatus according to claim 23 further comprising at least one additional connector, wherein the at least one additional connector is configured to be connected to at least one vessel selected from a group consisting of: a pulmonary artery and a pulmonary vein.

29. A heart preservation apparatus according to claim 28 wherein the at least one additional connector configured to be connected to the pulmonary artery connects to a lower end of the inclined trough.

30. A heart preservation apparatus according to claim 28 wherein the at least one additional connector configured to be connected to the pulmonary vein connects to an upper end of the inclined trough.

31. A heart preservation apparatus according to claim 23 further comprising a cover which, when in a closed position, combines with the housing to provide a sterile sealed enclosure.

32. A heart preservation apparatus according to claim 23 wherein the housing is made from a biocompatible polymer.

33. A heart preservation apparatus according to claim 23 wherein the at least one connector connects through a wall of the chamber to a perfusion circuit.

34. A heart preservation apparatus according to claim 23 wherein the concave cross-sectional shape of the inclined trough is v-shaped.

35. A heart preservation apparatus according to claim 23 wherein the concave cross-sectional shape of the inclined trough is u-shaped.

36. A heart preservation apparatus according to claim 23 wherein the inclined trough is defined by at least one wall at the upper end of the inclined trough and wherein the connector is coupled to the at least one wall.

37. A heart preservation apparatus according to claim 23 wherein the housing is defined by at least one wall at the upper end of the inclined trough and wherein the connector is coupled to the at least one wall.

* * * * *

UNITED STATES PATENT AND TRADEMARK OFFICE
CERTIFICATE OF CORRECTION

PATENT NO. : 7,572,622 B2
APPLICATION NO. : 10/640867
DATED : August 11, 2009
INVENTOR(S) : Hassanein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 899 days.

Signed and Sealed this

Seventh Day of September, 2010

David J. Kappos
*Director of the United States Patent and Trademark Office*